United States Patent
Stoltefuss et al.

(10) Patent No.: US 6,958,346 B2
(45) Date of Patent: Oct. 25, 2005

(54) 4-HETEROARYL-TETRAHYDROQUINOLINES AND THEIR USE AS INHIBITORS OF THE CHOLESTERIN-ESTER TRANSFER PROTEIN

(75) Inventors: Jürgen Stoltefuss, Haan (DE); Michael Lögers, Wuppertal (DE); Gunter Schmidt, Wuppertal (DE); Arndt Brandes, Wuppertal (DE); Carsten Schmeck, Wuppertal (DE); Klaus-Dieter Bremm, Wuppertal (DE); Hilmar Bischoff, Wuppertal (DE); Delf Schmidt, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 63 days.

(21) Appl. No.: 09/999,233

(22) Filed: Oct. 31, 2001

(65) Prior Publication Data

US 2002/0062024 A1 May 23, 2002

Related U.S. Application Data

(62) Division of application No. 09/508,399, filed as application No. PCT/EP98/05656 on Sep. 7, 1998.

(30) Foreign Application Priority Data

Sep. 18, 1997 (DE) .......................... 197 41 051

(51) Int. Cl.$^7$ .................. A61K 31/4709; C07D 401/08
(52) U.S. Cl. ......................... 514/278; 546/15
(58) Field of Search ............................. 546/15; 514/278

(56) References Cited

U.S. PATENT DOCUMENTS 5,169,857 A  12/1992  Angerbauer et al. ........ 514/344

FOREIGN PATENT DOCUMENTS

| EP | 0 304 063 | 2/1989 |
| EP | 0 325 230 | 7/1989 |
| EP | 0 818 197 | 1/1998 |
| WO | WO 9839299 | 9/1998 |

*Primary Examiner*—Patricia L Morris
(74) *Attorney, Agent, or Firm*—Norris McLaughlin & Marcus

(57) ABSTRACT

Hetero-tetrahydroquinolines can be prepared either by condensing correspondingly substituted hetero-tetrahydroquinoline aldehydes with the desired substituent or by reducing the corresponding keto-substituted hetero-tetrahydroquinolines, followed by introduction of the desired substituent by customary methods. The hetero-tetrahydroquinolines are suitable for use as active compounds in medicaments, in particular in medicaments for treating artheriosclerosis and dyslipidaemias.

8 Claims, No Drawings

4-HETEROARYL-TETRAHYDROQUINOLINES AND THEIR USE AS INHIBITORS OF THE CHOLESTERIN-ESTER TRANSFER PROTEIN

This application is a division of U.S. Ser. No. 09/508,399, now allowed, which was filed on Mar. 10, 2000, and is, in turn, a 371 of PCT/EP98/05656, which was filed on Sep. 7, 1998. Priority under 35 USC § 120 is claimed both to U.S. Ser. No. 09/508,399 and PCT/EP98/05656.

The present invention relates to hetero-tetrahydroquinolines, to processes for their preparation and to their use in medicaments.

The publication U.S. Pat. No. 5,169,857-A2 discloses 7-(polysubstituted pyridyl)-6-heptenoates for treating arteriosclerosis, lipoproteinaemia and hyperproteinaemia. Moreover, the preparation of 7-(4-aryl-3-pyridyl)-3,5-dihydroxy-6-heptenoates is described in the publication EP-325 130-A2. Furthermore, the compound 5(6H)-quinolone,3-benzyl-7,8-dihydro-2,7,7-trimethyl-4-phenyl is known from the publication Khim. Geterotsikl. Soedin. (1967), (6), 1118–1120.

The present invention relates to hetero-tetrahydroquinolines of the general formula (I):

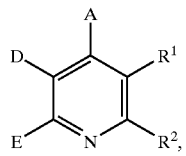
(I)

in which

A represents cycloalkyl having 3 to 8 carbon atoms or
  represents a 5- to 7-membered saturated, partially unsaturated or unsaturated, optionally benzo-fused heterocycle having up to 3 heteroatoms from the group consisting of S, N and O which, in the case of a saturated heterocycle with a nitrogen function, is optionally also attached via this function, and where the abovementioned ring systems are optionally substituted up to 5 times by identical or different substituents from the group consisting of halogen, nitro, hydroxyl, trifluoromethyl, trifluoromethoxy and straight-chain or branched alkyl, acyl, hydroxyalkyl or alkoxy having in each case up to 7 carbon atoms, or by a group of the formula —$NR^3R^4$,
  in which
    $R^3$ and $R^4$ are identical or different and represent hydrogen, phenyl or straight-chain or branched alkyl having up to 6 carbon atoms,
  or
A represents a radical of the formula:

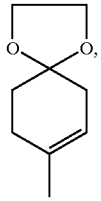

D represents aryl having 6 to 10 carbon atoms which is optionally substituted by phenyl, nitro, halogen, trifluoromethyl or trifluoromethoxy, or represents a radical of the formula:

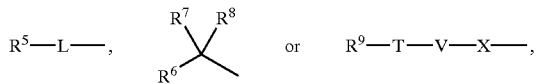

in which
$R^5$, $R^6$ and $R^9$ independently of one another represent cycloalkyl having 3 to 6 carbon atoms, or
  represent aryl having, 6 to 10 carbon atoms or represent a 5- to 7-membered optionally benzo-fused saturated or unsaturated mono-, bi- or tricyclic hetreocycle having up to 4 heteroatoms from the group consisting of S, N and O,
  where the cycles are optionally substituted, in the case of the nitrogen-containing rings also via the N function, up to 5 times by identical or different substituents from the group consisting of halogen, trifluoromethyl, nitro, hydroxyl, cyano, carboxyl, trifluoromethoxy, and straight-chain or branched acyl, alkyl, alkylthio, alkylalkoxy, alkoxy or alkoxycarbonyl having in each case up to 6 carbon atoms, by aryl or trifluoromethyl-substituted aryl having in each case 6 to 10 carbon atoms or by an optionally benzo-fused aromatic 5- to 7-membered heterocycle having up to 3 heteroatoms from the group consisting of S, N and O,
and/or by a group of the formula —$OR^{10}$, —$SR^{11}$, —$SO_2R^{12}$ or —$NR^{13}R^{14}$,
  in which
    $R^{10}$, $R^{11}$ and $R^{12}$ independently of one another represent aryl having 6 to 10 carbon atoms which for its part is substituted up to 2 times by identical or different substituents from the group consisting of phenyl, halogen and straight-chain or branched alkyl having up to 6 carbon atoms,
    $R^{13}$ and $R^{14}$ are identical or different and have the meaning of $R^3$ and $R^4$ given above,
  or
$R^5$ and/or $R^6$ represent(s) a radical of the formula:

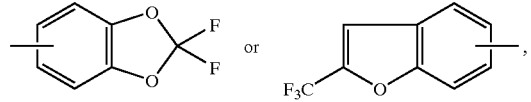

$R^7$ represents hydrogen or halogen,
and
$R^8$ represents hydrogen, halogen, azido, trifluoromethyl, hydroxyl, trifluoromethoxy, straight-chain or branched alkoxy or alkyl having in each case up to 6 carbon atoms or a radical of the formula —$NR^{15}R^{16}$,
  in which
    $R^{15}$ and $R^{16}$ are identical or different and have the meaning of $R^3$ and $R^4$ given above,
  or
$R^7$ and $R^8$ together form a radical of the formula =O or =$NR^{17}$,
  in which
    $R^{17}$ represents hydrogen or straight-chain or branched alkyl, alkoxy or acyl having in each case up to 6 carbon atoms,
L represents a straight-chain or branched alkylene or alkenylene chain having in each case up to 8 carbon atoms which are optionally substituted up to 2 times by hydroxyl, T and X are identical or different and represent a straight-chain or branched alkylene chain having up to 8 carbon atoms,
or
T or X represents a bond,
V represents an oxygen or sulphur atom or represents an —NR$^{18}$ group,
in which
R$^{18}$ represents hydrogen or straight-chain or branched alkyl having up to 6 carbon atoms or phenyl,
E represents cycloalkyl having 3 to 8 carbon atoms, or represents straight-chain or branched alkyl having up to 8 carbon atoms which is optionally substituted by cycloalkyl having 3 to 8 carbon atoms or hydroxyl, or represents phenyl which is optionally substituted by halogen or trifluoromethyl,
R$^1$ and R$^2$ together form a straight-chain or branched alkylene chain having up to 7 carbon atoms which has to be substituted by a carbonyl group and/or by a radical of the formula:

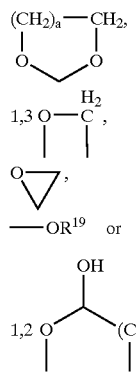

in which
a and b are identical or different and represent a number 1, 2 or 3,
R$^{19}$ represents hydrogen, cycloalkyl having 3 to 7 carbon atoms, straight-chain or branched silylalkyl having up to 8 carbon atoms or straight-chain or branched alkyl having up to 8 carbon atoms which is optionally substituted by hydroxyl, straight-chain or branched alkoxy having up to 6 carbon atoms or by phenyl which for its part may be substituted by halogen, nitro, trifluoromethyl, trifluoromethoxy or by phenyl or tetrazole-substituted phenyl,
and alkyl is optionally substituted by a group of the formula: —OR$^{22}$,
in which
R$^{22}$ represents straight-chain or branched acyl having up to 4 carbon atoms or benzyl,
or
R$^{19}$ represents straight-chain or branched acyl having up to 20 carbon atoms or benzoyl which is optionally substituted by halogen, trifluoromethyl, nitro or trifluoromethoxy, or
represents straight-chain or branched fluoroacyl having up to 8 carbon atoms and 9 fluorine atoms,
R$^{20}$ and R$^{21}$ are identical or different, represent hydrogen, phenyl or straight-chain or branched alkyl having up to 6 carbon atoms,
or R$^{20}$ and R$^{21}$ together form a 3 to 6-membered carbocycle
and, if appropriate also geminally, the carbocycles formed are optionally substituted up to 6 times by identical or different substituents from the group consisting of trifluoromethyl, hydroxyl, nitrile, halogen, carboxyl, nitro, azido, cyano, cycloalkyl or cycloalkyloxy having in each case 3 to 7 carbon atoms, straight-chain or branched alkoxycarbonyl, alkoxy or alkylthio having in each case up to 6 carbon atoms and straight-chain or branched alkyl having up to 6 carbon atoms which for its part is substituted up to 2 times by identical or different substituents from the group consisting of hydroxyl, benzyloxy, trifluoromethyl, benzoyl, straight-chain or branched alkoxy, oxyacyl or carboxyl having in each case up to 4 carbon atoms and phenyl which for its part may be substituted by halogen, trifluoromethyl or trifluoromethoxy,
and/or the carbocycles formed are optionally substituted, also seminally, up to 5 times by identical or different substituents from the group consisting of phenyl, benzoyl, thiophenyl and sulphonylbenzyl which for their part are optionally substituted by halogen, trifluoromethyl, trifluoromethoxy or nitro,
and/or are optionally substituted by a radical of the formula:

—SO$_2$—C$_6$H$_5$, —(CO)$_d$—NR$^{23}$R$^{24}$ or =O,
in which
c represents a number 1, 2, 3 or 4,
d represents a number 0 or 1,
R$^{23}$ and R$^{24}$ are identical or different and represent hydrogen, cycloalkyl having 3 to 6 carbon atoms, straight-chain or branched alkyl having up to 6 carbon atoms, benzyl or phenyl which is optionally substituted up to 2 times by identical or different substituents from the group consisting of halogen, trifluoromethyl, cyano, phenyl and nitro,
and/or the carbocycles formed are optionally substituted by a spiro-linked radical of the formula:

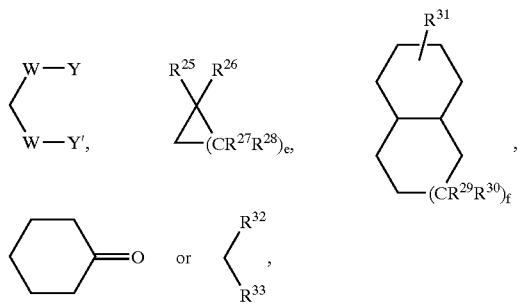

in which
W represents either an oxygen or a sulphur atom,
Y and Y' together form a 2- to 6-membered straight-chain or branched alkylene chain,
e represents a number 1, 2, 3, 4, 5, 6 or 7,
f represents a number 1 or 2,
R$^{25}$, R$^{26}$, R$^{27}$, R$^{28}$, R$^{29}$, R$^{30}$ and R$^{31}$ are identical or different and represent hydrogen, trifluoromethyl, phenyl, halogen or straight-chain or branched alkyl or alkoxy having in each case up to 6 carbon atoms, or $R^{25}$ and $R^{26}$ or $R^{27}$ and $R^{28}$ in each case together form a straight-chain or branched alkyl chain having up to 6 carbon atoms, or $R^{25}$ and $R^{26}$ or $R^{27}$ and $R^{28}$ in each case together form a radical of the formula:

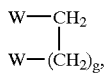

in which

W is as defined above, g represents a number 1, 2, 3, 4, 5, 6 or 7, $R^{32}$ and $R^{33}$ together form a 3- to 7-membered heterocycle which contains an oxygen or sulphur atom or a group of the formula SO, $SO_2$ or —$NR^{34}$, in which $R^{34}$ represents hydrogen, phenyl, benzyl or straight-chain or branched alkyl having up to 4 carbon atoms, and their salts and N-oxides.

The hetero-tetrahydroquinolines according to the invention can also be present in the form of their salts. In general, salts with organic or inorganic bases or acids may be mentioned here.

In the context of the present invention, preference is given to physiologically acceptable salts. Physiologically acceptable salts of the compounds according to the invention can be salts of the substances according to the invention with mineral acids, carboxylic acids or sulphonic acids. Particular preference is given, for example, to salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Particular preference is given, for example, to sodium salts, potassium salts, magnesium salts or calcium salts, and also to ammonium salts which are derived from ammonia or organic amines, such as, for example, ethylamine, di- or triethylamine, di- or triethanolamine, dicyclohexylamine, dimethylaminoethanol, arginine, lysine, ethylenediamine or 2-phenylethylamine.

The compounds according to the invention can exist in stereoisomeric forms which are either like image and mirror image (enantiomers), or which are not like image and mirror image (diastereomers). The invention relates both to the enantiomers or diastereomers and to their respective mixtures. These mixtures of the enantiomers and diastereomers can be separated into the stereoisomerically uniform components in a known manner.

In the context of the invention, a 3- to 8-membered saturated carbocyclic ring represents a cyclopropyl, cyclobutyl, cyclopentyl, cyclohexyl, cycloheptyl or cyclooctyl ring. Preference is given to a cyclopropyl, cyclobutyl, cyclopentyl or cyclohexyl ring. Particular preference is given to cyclobutyl, cyclopentyl or cyclohexyl.

In the context of the invention, heterocycle generally represents a saturated, partially unsaturated or unsaturated, optionally benzo-fused 5- to 7-membered, preferably 5- to 6-membered, heterocycle which may contain up to 3 heteroatoms from the group consisting of S, N and O. Examples which may be mentioned are:. indolyl, isoquinolyl, quinolyl, benzo[b]thiophene, benzo[b]furanyl, pyridyl, thienyl, furyl, pyrrolyl, thiazolyl, oxazolyl, imidazolyl, morpholinyl or piperidyl. Preference is given to quinolyl, furyl, pyridyl and thienyl.

Preference is given to the compounds of the general formula (I) according to the invention, in which A represents cyclopropyl, cyclobutyl, cyclopentyl, cycloheptyl, cyclooctyl or cyclohexyl, or represents thienyl, imidazolyl, pyrrole, furryl, pyridyl, morpholine, pyrimidyl or pyridazinyl, which are optionally substituted up to 2 times by identical or different substituents from the group consisting of fluorine, chlorine, bromine, amino, hydroxyl, trifluoromethyl, trifluoromethoxy and straight-chain or branched alkyl, and alkoxy having in each case up to 6 carbon atoms, or A represents a radical of the formula:

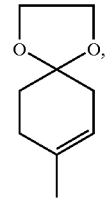

D represents phenyl which is optionally substituted by nitro, fluorine, chlorine, bromine, phenyl, trifluoromethyl or trifluoromethoxy, or represents a radical of the formula:

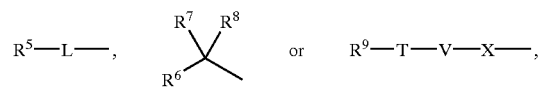

in which $R^5$, $R^6$ and $R^9$ independently of one another represent cyclopropyl, cyclopentyl or cyclohexyl, or represent phenyl, naphthyl, pyridyl, tetrazolyl, pyrimidyl, pyrazinyl, pyrrolidinyl, indolyl, morpholinyl, imidazolyl, benzothiazolyl, phenoxathiin-2-yl, benzoxazolyl, furyl, quinolyl or purin-8-yl, where the cycles are optionally substituted up to 3 times, in the case of the nitrogen-containing rings also via the N function, by identical or different substituents from the group consisting of fluorine, chlorine, bromine, trifluoromethyl, hydroxyl, cyano, carboxyl, trifluoromethoxy, straight-chain or branched acyl, alkyl, alkylthio, alkylalkoxy, alkoxy or alkoxycarbonyl having in each case up to 4 carbon atoms, triazolyl, tetrazolyl, benzoxathiazolyl, trifluoromethyl-substituted phenyl and phenyl, or $R^7$ represents hydrogen, fluorine, chlorine or bromine, and $R^8$ represents hydrogen, fluorine, chlorine, bromine, azido, trifluoromethyl, hydroxyl, trifluoromethoxy, straight-chain or branched alkoxy or alkyl having in each case up to 5 carbon atoms or a radical of the formula —$NR^{15}R^{16}$, in which $R^{15}$ and $R^{16}$ are identical or different and represent hydrogen, phenyl or straight-chain or branched alkyl having up to 4 carbon atoms, or $R^7$ and $R^8$ together form a radical of the formula =O or =NR$^{17}$, in which $R^{17}$ represents hydrogen or straight-chain or branched alkyl, alkoxy or acyl having in each case up to 4 carbon atoms, L represents a straight-chain or branched alkylene or alkenylene chain having in each case up to 6 carbon atoms which are optionally substituted up to 2 times by hydroxyl, T and X are identical or different and represent a straight-chain or branched alkylene chain having up to 6 carbon atoms, or T or X represents a bond, V represents an oxygen or sulphur atom or represents a group of the formula —NR$^{18}$—, in which $R^{18}$ represents hydrogen or straight-chain or branched alkyl having up to 4 carbon atoms or phenyl, E represents cyclopropyl, -butyl, -pentyl, -hexyl or -heptyl, or represents straight-chain or branched alkyl having up to 6 carbon atoms which is optionally substituted by cyclopropyl, -butyl, -hexyl, -pentyl, -heptyl or by hydroxyl, or represents phenyl which is optionally substituted by fluorine, chlorine or trifluoromethyl, $R^1$ and $R^2$ together form a straight-chain or branched alkylene chain having up to 6 carbon atoms which has to be substituted by a carboxyl group and/or by a radical of the formula:

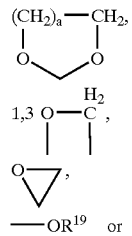

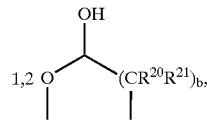

—OR$^{19}$ or

OH
|
1,2 O—(CR$^{20}$R$^{21}$)$_b$, in which a and b are identical or different and represent a number 1, 2 or 3, $R^{19}$ represents hydrogen, cyclopropyl, cyclopentyl, cyclohexyl, straight-chain or branched silylalkyl having up to 7 carbon atoms or straight-chain or branched alkyl having up to 6 carbon atoms which is optionally substituted by hydroxyl, straight-chain or branched alkoxy having up to 4 carbon atoms or by phenyl which for its part may be substituted by fluorine, chlorine, bromine, nitro, trifluoromethyl, trifluoromethoxy or by phenyl or tetrazole-substituted phenyl, and alkyl is optionally substituted by a group of the formula —OR$^{22}$, in which $R^{22}$ represents straight-chain or branched acyl having up to 3 carbon atoms or benzyl, or $R^{19}$ represents straight-chain or branched acyl having up to 18 carbon atoms or benzoyl which is optionally substituted by fluorine, chlorine, bromine, trifluoromethyl, nitro or trifluoromethoxy, or represents straight-chain or branched fluoroacyl having up to 6 carbon atoms, $R^{20}$ and $R^{21}$ are identical or different, represent hydrogen, phenyl or straight-chain or branched alkyl having up to 4 carbon atoms, or $R^{20}$ and $R^{21}$ together form a cyclopropyl, cyclobutyl, cyclopentyl, cyclohexyl or cycloheptyl ring, and the carbocycles formed are optionally substituted, if appropriate, also geminally, up to 5 times by identical or different substituents from the group consisting of trifluoromethyl, hydroxyl, carboxyl, azido, fluorine, chlorine, bromine, nitro, cyano, cyclopropyl, cyclobutyl, cyclopentyl, cyclohexyl, cyclopropyloxy, cyclopentyloxy, cyclohexyloxy, straight-chain or branched alkoxycarbonyl, alkoxy or alkylthio having in each case up to about 5 carbon atoms and straight-chain or branched alkyl having up to 5 carbon atoms which for its part is substituted up to 2 times by identical or different substituents from the group consisting of hydroxyl, benzyloxy, benzoyl, straight-chain or branched alkoxy or oxyacyl having in each case up to 3 carbon atoms, trifluoromethyl and phenyl which for its part may be substituted by fluorine, chlorine, bromine, trifluoromethyl or trifluoromethoxy, and/or the carbocycles formed are optionally substituted, also geminally, up to 4 times by identical or different substituents from the group consisting of phenyl, benzoyl, thiophenyl and sulphonylbenzyl which for their part are optionally substituted by fluorine, chlorine, bromine, trifluoromethyl, trifluoromethoxy or nitro, and/or are optionally substituted by a radical of the formula:

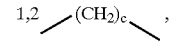

—SO$_2$C$_6$H$_5$, —(CO)$_d$—NR$^{23}$R$^{24}$ or =O, in which c represents a number 1, 2, 3 or 4, d represents a number 0 or 1, $R^{23}$ and $R^{24}$ are identical or different and represent hydrogen, cyclopropyl, cyclobutyl, cyclopentyl, cyclohexyl, straight-chain or branched alkyl having up to 5 carbon atoms, benzyl or phenyl which is optionally substituted by fluorine, chlorine, bromine, phenyl or trifluoromethyl, and/or the carbocycles formed are optionally substituted by a spiro-linked radical of the formula:

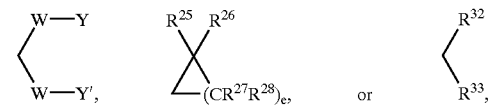

in which

W represents either an oxygen or a sulphur atom,

Y and Y' together form a 2- to 5-membered straight-chain or branched alkyl chain, e represents a number 1, 2, 3, 4, 5 or 6, f represents a number 1 or 2, $R^{25}$, $R^{26}$, $R^{27}$ and $R^{28}$ are identical or different and represent hydrogen, trifluoromethyl, phenyl, fluorine, chlorine, bromine or straight-chain or branched alkyl or alkoxy having in each case up to 5 carbon atoms, or $R^{25}$ and $R^{26}$ or $R^{27}$ and $R^{28}$ in each case together form a straight-chain or branched alkyl chain having up to 5 carbon atoms or or $R^{25}$ and $R^{26}$ or $R^{27}$ and $R^{28}$ in each case together form a radical of the formula:

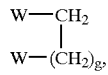

in which

W is as defined above, g represents a number 1, 2, 3, 4, 5 or 6, and their salts and N-oxides.

Particular preference is given to compounds of the general formula (I) according to the invention, in which A represents cyclopropyl, cyclopentyl or cyclohexyl, or represents thienyl or pyridyl which are optionally substituted up to 2 times by identical or different substituents from the group consisting of fluorine, chlorine, bromine, hydroxyl, trifluoromethyl, trifluoromethoxy and straight-chain or branched alkyl or alkoxy having in each case up to 5 carbon atoms, or A represents a radical of the formula:

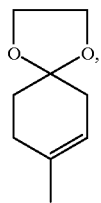

D represents phenyl which is optionally substituted by nitro, trifluoromethyl, phenyl, fluorine, chlorine or bromine, or represents a radical of the formula:

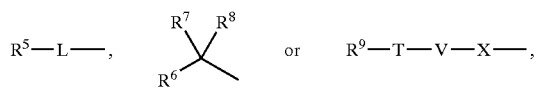

in which $R^5$, $R^6$ and $R^9$ independently of one another represent cyclopropyl, cyclopentyl or cyclohexyl, or represent phenyl, naphthyl or pyridyl, where the cycles optionally up to 2times by identical or different substituents from the group consisting of fluorine, chlorine, trifluoromethyl, hydroxyl, cyano, carboxyl, trifluoromethoxy and straight-chain or branched alkyl, alkylthio, alkylalkoxy, alkoxy or alkoxycarbonyl having in each case up to 4 carbon atoms, or $R^7$ represents hydrogen or fluorine, and $R^8$ represents hydrogen, fluorine, chlorine, bromine, azido, trifluoromethyl, hydroxyl, trifluoromethoxy, or straight-chain or branched alkoxy or alkyl having in each case up to 4 carbon atoms or a radical of the formula $-NR^{15}R^{16}$, in which $R^{15}$ and $R^{16}$ are identical or different and represent hydrogen or straight-chain or branched alkyl having up to 3 carbon atoms, or $R^7$ and $R^8$ together represent a radical of the formula =O, L represents a straight-chain or branched alkylene or alkenylene chain having in each case up to 5 carbon atoms which are optionally substituted up to 2 times by hydroxyl, T and X are identical or different and represent a straight-chain or branched alkylene chain having up to 3 carbon atoms, or T or X represents a bond, V represents an oxygen or sulphur atom or a group of the formula $-NR^{18}$, in which $R^{18}$ represents hydrogen or straight-chain or branched alkyl having up to 3 carbon atoms, E represents cyclopropyl, cyclopentyl or cyclohexyl or phenyl which is optionally substituted by fluorine or trifluoromethyl, or represents straight-chain or branched alkyl having up to 4 carbon atoms which is optionally substituted by hydroxyl, $R^1$ and $R^2$ together form a straight-chain or branched alkylene chain having up to 5 carbon atoms which has to be substituted by a carbonyl group and/or a radical of the formula $-OR^{19}$, in which $R^{19}$ represents hydrogen, cyclopropyl, cyclopentyl or cyclohexyl, or $R^{19}$ represents straight-chain or branched acyl having up to 15 carbon atoms or benzoyl which is optionally substituted by fluorine, chlorine, bromine, trifluoromethyl, nitro or trifluoromethoxy, or represents a radical of the formula $-Si(CH_3)_2C(CH_3)_3$, and the carbocycles formed are optionally substituted, if appropriate also geminally, up to 4 times by identical or different substituents from the group consisting of fluorine, hydroxyl, trifluoromethyl, carboxyl, azido, chlorine, bromine, nitro, cyano, cyclopropyl, cyclobutyl, cyclopentyl, cyclohexyl, cyclopropyloxy, cyclopentyloxy, cyclohexyloxy, straight-chain or branched alkoxycarbonyl, alkoxy or alkylthio having in each case up to 4 carbon atoms and straight-chain or branched alkyl having up to 4 carbon atoms which for its part is substituted up to 2 times by identical or different substituents from the group consisting of hydroxyl, benzyloxy, trifluoromethyl, benzoyl, methoxy, oxyacetyl and phenyl which for its part may be substituted by fluorine, chlorine, bromine, trifluoromethyl or trifluoromethoxy, and/or the carbocycles formed are optionally substituted, also geminally, up to 4 times by identical or different substituents from the group consisting of phenyl, benzoyl, thiophenyl and sulphonylbenzyl which for their part are optionally substituted by fluorine, trifluoromethyl, trifluoromethoxy or nitro, and/or are optionally substituted by a radical of the formula:

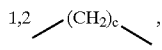

or =O,
in which
c represents a number 1, 2, 3 or 4,
and/or the carbocycles formed are optionally substituted by a spiro-linked radical of the formula:

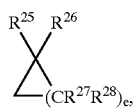

in which
e represents a number 1, 2, 3, 4 or 5,
$R^{25}$, $R^{26}$, $R^{27}$ and $R^{28}$ are identical or different and represent hydrogen, trifluoromethyl, phenyl, fluorine, chlorine, bromine or straight-chain or branched alkyl or alkoxy having in each case up to 4 carbon atoms,
or
$R^{25}$ and $R^{26}$ or $R^{27}$ and $R^{28}$ together form a straight-chain or branched alkyl chain having up to 4 carbon atoms,
and their salts and N-oxides.

Very particular preference is given to compounds of the general formula (I) according to the invention,
in which
A represents cyclopropyl, cyclopentyl or cyclohexyl, or represents thienyl or pyridyl, or A represents a radical of the formula:

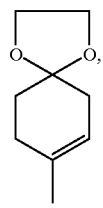

D represents phenyl which is optionally substituted by trifluoromethyl, fluorine, or
represents a radical of the formula:

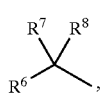

in which
$R^6$ represents phenyl which is optionally substituted by fluorine, chlorine, trifluoromethyl, trifluoromethoxy, straight-chain or branched alkyl having in each case up to 4 carbon atoms, or
$R^7$ represents hydrogen or fluorine,
and
$R^8$ represents hydrogen, fluorine, chlorine, hydroxyl, methoxy or
$R^7$ and $R^8$ together represent a radical of the formula =O,
E represents cyclopropyl, cyclopentyl or cyclohexyl represents straight-chain or branched alkyl having up to 4 carbon atoms,
$R^1$ and $R^2$ together form a straight-chain or branched alkylene chain having up to 5 carbon atoms which has to be substituted by a carbonyl group and/or a radical of the formula —$OR^{19}$,
in which
$R^{19}$ represents hydrogen
or represents a radical of the formula —$Si(CH_3)_2C(CH_3)_3$,
and their salts and N-oxides.

Moreover, processes for preparing the compounds of the general formula (I) according to the invention have been found, characterized in that

[A] in the case where D≠aryl, compounds of the general formula (II):

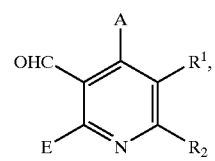

(II)

in which
A, E, $R^1$ and $R^2$ are as defined above,
with organometallic reagents in a Grignard or Wittig reaction or in a reaction with organolithium compounds, the substituent D is synthesized in inert solvents,
or in the case where D represents the radical of the formula $R^9$-T-V—X in which V is an oxygen atom,
[B] either compounds of the general formula (III):

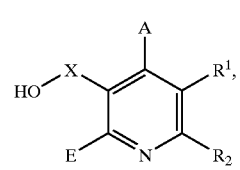

(III)

in which
A, E, X, $R^1$ and $R^2$ are as defined above,
are reacted with compounds of the general formula (IV):

(IV), in which
$R^9$ and T are as defined above
and
Z represents halogen, preferably chlorine or bromine,
in inert solvents, if appropriate in the presence of a base and/or auxiliary, or

[C] compounds of the general formula (III) are initially, by reaction with compounds of the general formula (V):

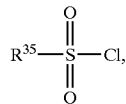
(V)

in which
R³⁵ represents straight-chain alkyl having up to 4 carbon atoms,
converted into the compounds of the general formula (VI):

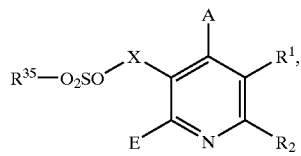
(VI)

in which
A, E, X, R¹, R² and R³⁵ are as defined above,
and subsequently reacted with compounds of the general formula (VII):

(VII), in which
R⁹, T and V are as defined above,
and, if appropriate, protective groups are removed,
or

[D] in the case of the compounds of the general formula (Ia):

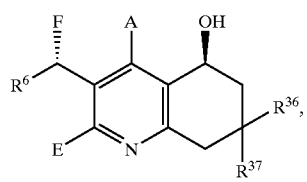
(Ia)

in which
A and R⁶ are as defined above,
R³⁶ and R³⁷ are identical or different and
   represent cycloalkyl or cycloalkyloxy having in each case 3 to 7 carbon atoms, or
   represent straight-chain or branched alkyl having up to 6 carbon atoms, or
   represent phenyl which for its part are optionally substituted by halogen, trifluoromethyl, trifluoromethoxy or nitro, or
R³⁶ and R³⁷ represent one of the abovementioned spiro-linked radicals of the formula:

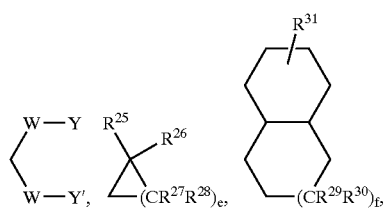

-continued

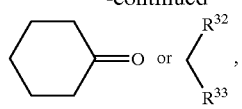

in which
W, Y, Y', R²⁵, R²⁶, R²⁷, R²⁸, e, R²⁹, R³⁰, R³¹, R³² and R³³ are as defined above,
compounds of the general formula (VIII):

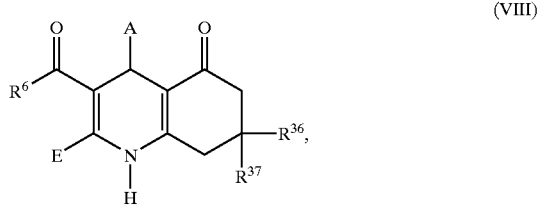
(VIII)

in which
R⁶, R³⁶, R³⁷, A and E are as defined above,
are initially oxidized to the compounds of the general formula (IX):

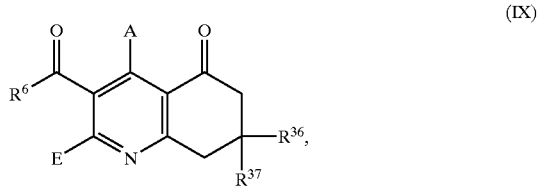
(IX)

in which
R⁶, R³⁶, R³⁷, A and E are as defined above,
these are, in a subsequent step, converted by asymmetric reduction into the compounds of the general formula (X):

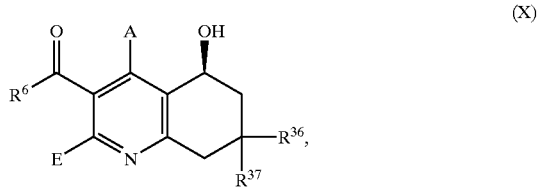
(X)

in which
R⁶, R³⁶, R³⁷, A and E are as defined above,
these are then converted, by the introduction of a hydroxyl protective group, into the compounds of the general formula (XI):

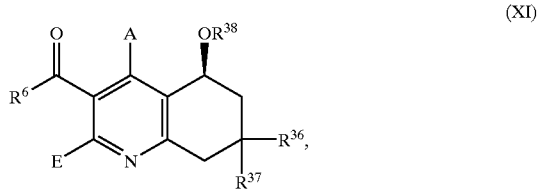
(XI)

in which
R⁶, R³⁶, R³⁷, A and E are as defined above
and
R³⁸ represents a hydroxyl protective group, preferably a radical of the formula —SiR³⁹R⁴⁰R⁴¹, in which $R^{39}$, $R^{40}$ and $R^{41}$ are identical or different and represent $C_1$–$C_4$-alkyl, which is used to prepare in a subsequent step, by diastereoselective reduction, the compounds of the general formula (XII):

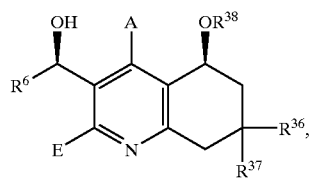

(XII)

in which $R^6$, $R^{36}$, $R^{37}$, $R^{38}$, A and E are as defined above, and the compounds of the general formula (XIII):

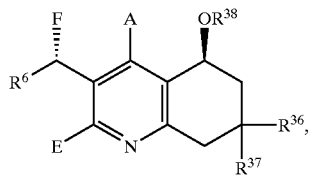

(XIII)

in which $R^6$, $R^{36}$, $R^{37}$, $R^{38}$, A and E are as defined above, are subsequently prepared by introducing the fluorine substituent with fluorinating agents, such as, for example, DAST and $SF_4$ derivatives, and the hydroxyl protective group is then removed by customary methods, and, if appropriate, the substituents listed under D, E and/or $R^1$ and $R^2$ are varied or introduced by customary methods.

By way of example, the processes according to the invention can be illustrated by the following schemes:

[A]

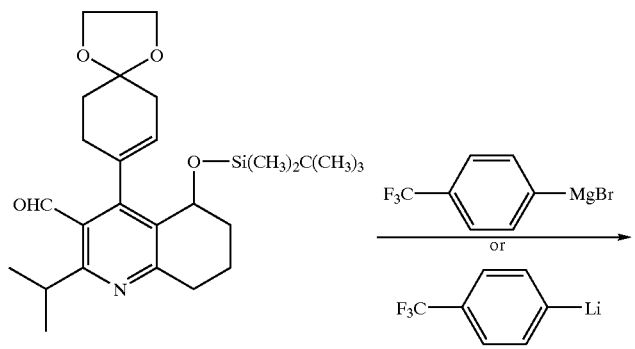

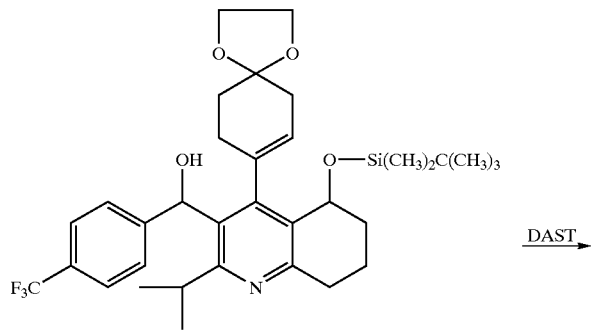

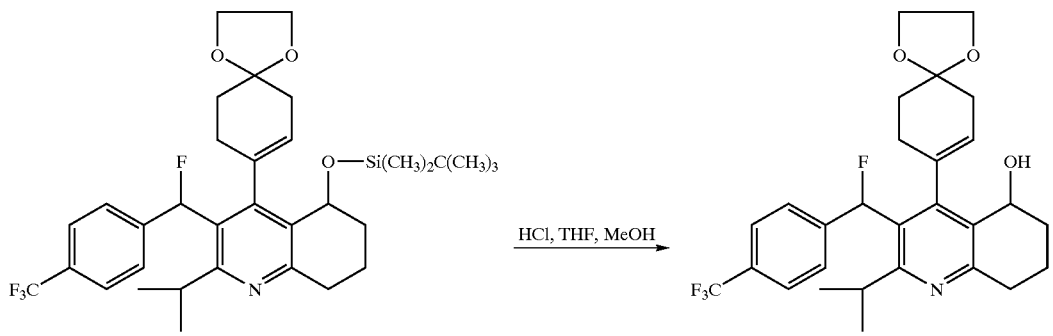

-continued
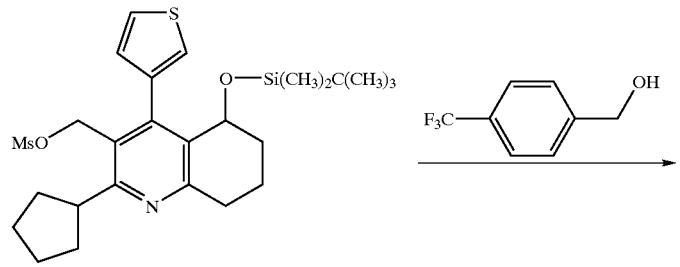
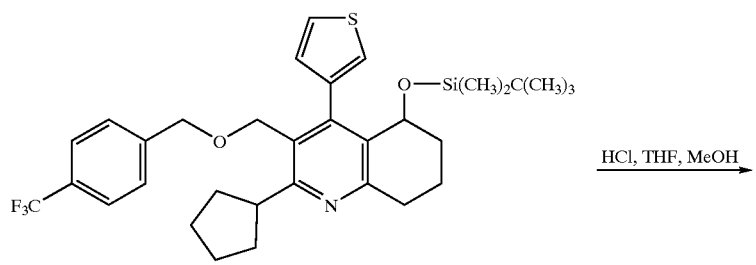
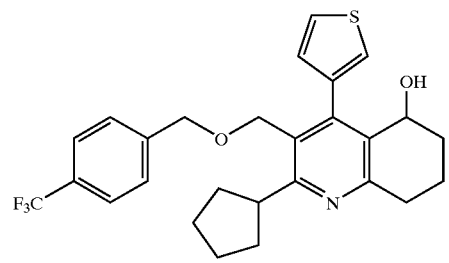
Ms = mesylate
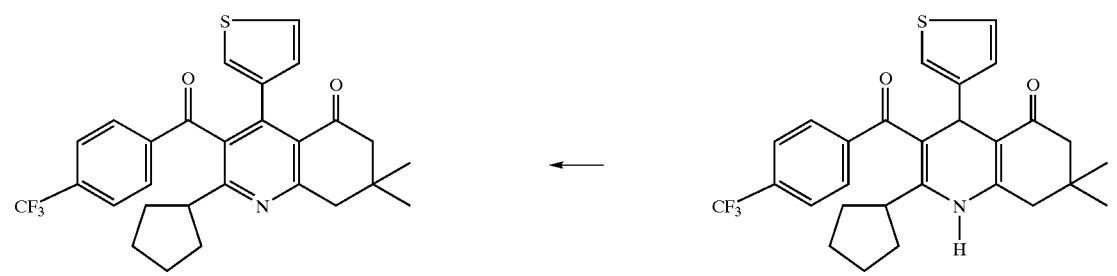
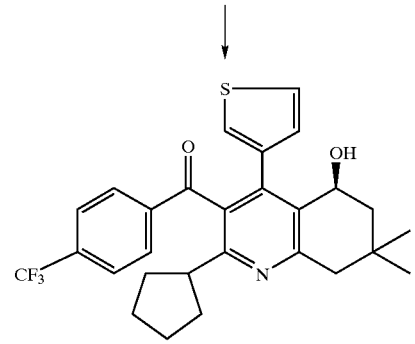
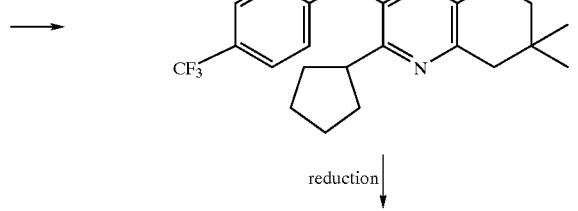
reduction -continued

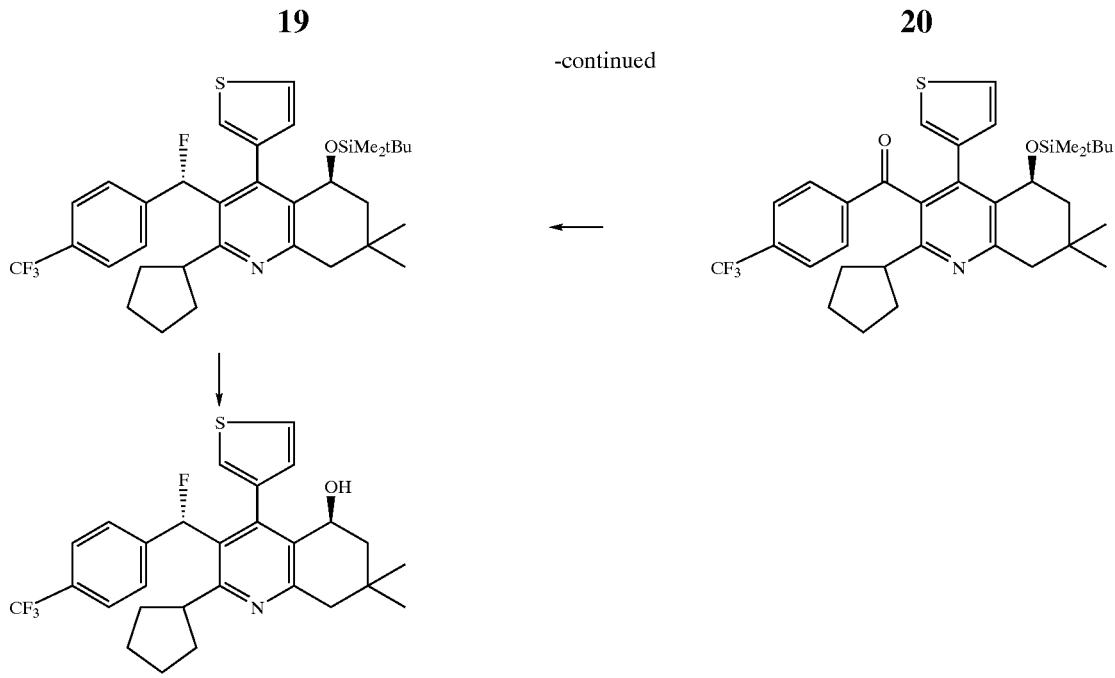

Suitable solvents for all processes are ethers such as diethyl ether, dioxane, tetrahydrofuran, glycol dimethyl ether, or hydrocarbons such as benzene, toluene, xylene, hexane, cyclohexane or mineral oil fractions, or halogenated hydrocarbons such as dichloromethane, trichloromethane, carbon tetrachloride, dichloroethylene, trichloroethylene or chlorobenzene, or ethyl acetate, or triethylamine, pyridine, dimethyl sulphoxide, dimethylformamide, hexamethylphosphoric triamide, acetonitrile, acetone or nitromethane. It is also possible to use mixtures of the solvents mentioned. Preference is given to dichloromethane.

Suitable bases for the individual steps are the customary strongly basic compounds. These preferably include organolithium compounds such as, for example, N-butyllithium, sec-butyllithium, tertbutyllithium or phenyllithium, or amides such as, for example, lithium diisopropylamide, sodium amide or potassium amide, or lithium hexamethylsilylamide, or alkali metal hydrides such as sodium hydride or potassium hydride. Particular preference is given to using N-butyllithium, sodium hydride or lithium diisopropylamide.

Suitable for the processes [B] and [C] are furthermore the customary inorganic bases. These preferably include alkali metal hydroxides or alkaline earth metal hydroxides, such as, for example, sodium hydroxide, potassium hydroxide or barium hydroxide, or alkali metal carbonates such as sodium carbonate or potassium carbonate or sodium bicarbonate. Particular preference is given to using sodium hydride or potassium hydroxide.

Suitable organometallic reagents are, for example, systems such as Mg/bromobenzotrifluoride and p-trifluoromethylphenyllithium.

The reductions are generally carried out with reducing agents, preferably those which are suitable for reducing ketones to hydroxyl compounds are. Particularly suitable for this purpose is the reduction with metal hydrides or complex metal hydrides in inert solvents, if appropriate in the presence of a trialkylborane. The reduction is preferably carried out using complex metal hydrides such as, for example, lithium borohydrides, sodium borohydrides, potassium borohydrides, zinc borohydrides, lithium trialkylborohydride, diisobutylaluminum hydride or lithium aluminum hydride. The reaction is very particularly preferably carried out using diisobutylaluminum hydride and sodium borohydride.

The reducing agent is generally employed in an amount of from 1 mol to 6 mol, preferably from 1 mol to 4 mol, based on 1 mol of the compounds to be reduced.

The reduction generally proceeds in a temperature range of from −78° C. to +50° C., preferably of from −78° C. to 0° C. in the case of DIBAH, of from 0° C. to room temperature in the case of NaBH$_4$, particularly preferably at −78° C., in each case depending on the choice of reducing agent and solvent.

The reduction generally proceeds at atmospheric pressure; however, it is also possible to carry out the reduction at elevated or reduced pressure.

In the case [A], the process is preferably carried out using initially compounds of the general formula (II) in which the carbocycle $R^1/R^2$ is initially only substituted by a group —OSiR′R″R‴ in which R′, R″ and R‴ are identical or different and represent phenyl or straight-chain or branched alkyl having up to 5 carbon atoms, and the substituent mentioned above under $R^{19}/R^{20}$ is introduced by customary methods after the protective group has been removed.

Removal of the protective group is generally carried out in one of the abovementioned alcohols and THF, preferably methanol/THF, in the presence of hydrochloric acid in a temperature range of from 0° C. to 50° C., preferably at room temperature, and at atmospheric pressure. In particular cases, preference is given to removing the protective group with tetrabutylammonium fluoride (TBAF) in THF.

In the context of the definition given above, hydroxyl protective group generally represents a protective group from the group trimethylsilyl, triisopropylsilyl, tert-butyl-dimethylsilyl, benzyl, benzyloxycarbonyl, 2-nitrobenzyl, 4-nitrobenzyl, tert-butyloxycarbonyl, allyloxycarbonyl, 4-methoxybenzyl, 4-methoxybenzyloxycarbonyl, tetrahydropyranyl, formyl, acetyl, trichloroacetyl, 2,2,2-trichloroethoxycarbonyl, methoxyethoxymethyl, [2-(trimethylsilyl)ethoxy]methyl, benzoyl, 4-methylbenzoyl, 4-nitrobenzoyl, 4-fluorobenzoyl, 4-chlorobenzoyl or 4-methoxybenzoyl. Preference is given to tetrahydropyranyl, tertbutyldimethylsilyl and triisopropylsilyl. Particular preference is given to tertbutyldimethylsilyl.

Suitable solvents for the individual steps are ethers such as diethyl ether, dioxane, tetrahydrofuran, glycol dimethyl ether, diisopropyl ether or hydrocarbons such as benzene, toluene, xylene, hexane, cyclohexane or mineral oil fractions, or halogenated hydrocarbons such as dichloromethane, trichloromethane, carbon tetrachloride, dichloroethylene, trichloroethylene or chlorobenzene. It is also possible to use mixtures of the solvents mentioned.

Suitable oxidizing agents for preparing the compounds of the general formula (IX) are, for example, nitric acid, cerium (IV) ammonium nitrate, 2,3-dichloro-5,6-dicyanobenzoquinone, pyridinium chlorochromate (PCC), pyridinium chlorochromate on basic alumina, osmium tetroxide and manganese dioxide. Preference is given to manganese dioxide and nitric acid.

The oxidation is carried out in one of the abovementioned chlorinated hydrocarbons and water. Preference is given to dichloromethane and water.

The oxidizing agent is employed in an amount of from 1 mol to 10 mol, preferably from 2 mol to 5 mol, based on 1 mol of the compounds of the general formula (VIII).

The oxidation generally proceeds at a temperature of from −50° C. to +100° C., preferably from 0° C. to room temperature.

The oxidation generally proceeds at atmospheric pressure. However, it is also possible to carry out the oxidation at elevated or reduced pressure.

The asymmetric reduction to the compounds of the general formula (X) is generally carried out in one of the abovementioned ethers or toluene, preferably tetrahydrofuran and toluene.

The reduction is generally carried out using enantiomerically pure 1R,2S-aminoindanol and borane complexes such as $BH_3 \times THF$, $BH_3 \times DMS$ and $BH_3 \times (C_2H_5)_2NC_6H_5$. Preference is given to the system borane-diethylaniline/1R,2S-aminoindanol.

The reducing agent is generally employed in an amount of from 1 mol to 6 mol, preferably from 1 mol to 4 mol, based on 1 mol of the compounds to be reduced.

The reduction generally proceeds at a temperature of from −78° C. to +50° C., preferably from 0° C. to 30° C.

The reduction generally proceeds at atmospheric pressure; however, it is also possible to carry out the reduction at elevated or reduced pressure.

The hydroxyl protective group is introduced in one of the abovementioned hydrocarbons, dimethylformamide or THF, preferably in toluene in the presence of lutidine in a temperature range of from −20° C. to +50° C., preferably from −5° C. to room temperature and at atmospheric pressure.

General reagents for introducing the silyl protective group are tert-butyldimethylsilyl chloride or tert-butyldimethylsilyl trifluoromethanesulphonate. Preference is given to tert-butyldimethylsilyl trifluoromethanesulphonate.

The reduction to the compounds of the general formula (XII) proceeds in one of the abovementioned hydrocarbons, preferably toluene.

The reduction to prepare the compounds of the general formula (XII) is generally carried out using customary reducing agents, preferably those which are suitable for reducing ketones to hydroxyl compounds. Particularly suitable for this purpose is the reduction with metal hydrides or complex metal hydrides in the abovementioned inert solvents, such as, for example, toluene, if appropriate in the presence of a trialkylborane. The reduction is preferably carried out using complex metal hydrides such as, for example, lithium borohydride, sodium borohydride, potassium borohydride, zinc borohydride, lithium trialkylborohydride, diisobutylaluminum hydride, sodium bis-(2-methoxyethoxy)aluminum hydride or lithium aluminum hydride. The reduction is very particularly preferably carried out using sodium bis-(2-methoxyethoxy)aluminum hydride.

The reducing agent is generally employed in an amount of from 1 mol to 6 mol, preferably from 1 mol to 3 mol, based on 1 mol of the compounds to be reduced.

The reduction generally proceeds at a temperature of from −20° C. to +110° C., preferably from 0° C. to room temperature.

The reduction generally proceeds at atmospheric pressure; however, it is also possible to carry out the reduction at elevated or reduced pressure.

In the reduction to the compounds of the general formula (XII), small residues of the wrong diastereomer remain in the mother liquor. These residues can be reoxidized with customary oxidizing agents such as, for example, pyridinium chlorochromate (PCC) or activated manganese dioxide, in particular with activated manganese dioxide, to give protected (XI) and thus be recycled into the synthesis cycle without any loss in yield.

The fluorine substituent is generally introduced in one of the abovementioned hydrocarbons or methylene chloride, preferably in toluene and under an atmosphere of protective gas.

Under $SF_4$ derivatives, in general diethylamino sulphur trifluoride or 2,2'-bisfluoro-substituted amines such as, for example, diethyl-1,2,3,3,3-hexafluoropropylamine are prepared.

The reaction generally proceeds at a temperature of from −78° C. to 100° C., in the case of dimethylamino sulphur trifluoride preferably at from −78° C. to RT and in the case of diethyl-1,1,2,3,3,3-hexafluoropropylamine preferably at from room temperature to 80° C.

The protective group is generally removed in one of the abovementioned alcohols and THF, preferably methanol/THF in the presence of hydrochloric acid in a temperature range of from 0° C. to 50° C., preferably at room temperature, and atmospheric pressure. In particular cases, preference is given to removing the protective group with tetrabutylammonium fluoride (TBAF) in THF at room temperature.

The following types of reaction may be mentioned by way of example for derivatizations:

oxidations, reductions, hydrogenations, halogenation, Wittig/Grignard reactions and amidations/sulphoamidations.

Suitable bases for the individual steps are the customary strongly basic compounds. These preferably include organolithium compounds such as, for example, n-butyllithium, sec-butyllithium, tertbutyllithium or phenyllithium, or amides such as, for example, lithium diisopropylamide, sodium amide or potassium amide, or lithium hexamethylsilylamide, or alkali metal hydrides such as sodium hydride or potassium hydride. Particular preference is given to using N-butyllithium, sodium hydride or lithium diisopropylamide.

Suitable bases are furthermore the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium bicarbonate. Particular preference is given to using sodium hydroxide or potassium hydroxide.

Suitable solvents for the individual reaction steps are also alcohols such as methanol, ethanol, propanol, butanol or tertbutanol. Preference is given to tertbutanol.

If required, it may be necessary to carry out some reaction steps under an atmosphere of protective gas.

The halogenations are generally carried out in one of the abovementioned chlorinated hydrocarbons, preference being given to methylene chloride.

Suitable halogenating agents are, for example, diethylamino sulphur trifluoride (DAST), morpholino sulphur trifluoride or $SOCl_2$.

The halogenation generally proceeds in a temperature range of from −78° C. to +50° C., preferably from −78° C. to 0° C., in each case depending on the choice of the halogenating agent and the solvent.

The halogenation generally proceeds at atmospheric pressure; however, it is also possible to carry out the halogenation at elevated or reduced pressure.

The compounds of the general formulae (II) and (III) are novel, and they can be prepared by preparing,
by reaction of the compounds of the general formula (XIV):

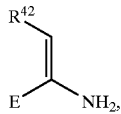

(XIV)

in which
E is as defined above
and
$R^{42}$ represents $C_1$–$C_4$-alkoxycarbonyl or aryl (D=aryl)
with aldehydes of the general formula (XV):

A-CHO  (XV), in which
A is as defined above
and compounds of the general formula (XVI):

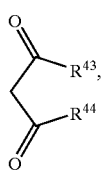

(XVI)

in which
$R^{43}$ and $R^{44}$, together with a carbonyl group, embrace the scope of the meaning of $R^1$ and $R^2$ mentioned above,
the compounds of the general formula (XVII):

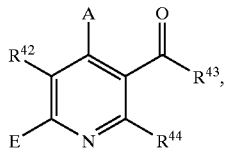

(XVII)

in which
A, E, $R^{42}$, $R^{43}$ and $R^{44}$ are as defined above
and, in the case of the compounds of the general formula (III), carrying out a reduction, as described above, to furnish the hydroxymethyl function
and, in a last step, converting the alkoxycarbonyl group ($R^{42}$) by a reduction-oxidation sequence into an aldehyde group.

Solvents which are suitable for the oxidation are ethers such as diethyl ether, dioxane, tetrahydrofuran, glycol dimethyl ether, or hydrocarbons such as benzene, toluene, xylene, hexane, cyclohexane or mineral oil fractions, or halogenated hydrocarbons such as dichloromethane, trichloromethane, carbon tetrachloride, dichloroethylene, trichloroethylene or chlorobenzene, or ethyl acetate, or triethylamine, pyridine, dimethyl sulphoxide, dimethylformamide, hexamethylphosphoric triamide, acetonitrile, acetone or nitromethane. It is also possible to use mixtures of the solvents mentioned. Preference is given to methylene chloride.

Suitable oxidizing agents are, for example, cerium (IV) ammonium nitrate, 2,3-dichloro-5,6-dicyano-benzoquinone, pyridinium chlorochromate (PCC), pyridinium chlorochromate on basic alumina, osmium tetroxide and manganese dioxide. Preference is given to sulphur trioxide-pyridine complex in DMSO/methylene chloride and pyridinium chlorochromate on basic alumina.

The oxidizing agent is employed in an amount of from 1 mol to 10 mol, preferably from 2 mol to 5 mol, based on 1 mol of the compounds of the general formula (XVII).

The oxidation generally proceeds in a temperature range of from −50° C. to +100° C., preferably from 0° C. to room temperature.

The oxidation generally proceeds at atmospheric pressure. However, it is also possible to carry out the oxidation at elevated or reduced pressure.

The compounds of the general formulae (IV), (V), (VII), (XIV), (XV) and (XVI) are known per se or can be prepared by customary methods.

Some of the compounds of the general formulae (VI) and (XV) are known, or they are novel, in which case they can be prepared as described above.

The compounds of the general formulae (IX) and (X) are novel species and can be prepared as described above.

The compounds of the general formula (VIII) are novel and can be prepared by reacting compounds of the general formulae (XVa), (XVIII) and (XIX):

A-CHO  (XVa),

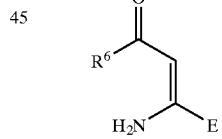

(XVIII)

and

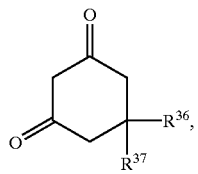

(XIX)

in which
A, E, $R^6$, $R^{36}$ and $R^{37}$ are as defined above in the presence of an acid.

Suitable solvents for preparing the compounds of the general formula (VIII) are the abovementioned ethers or alcohols. Preference is given to diisopropyl ether.

Suitable acids for preparing the compounds of the general formula (VIII) are, in general, organic carboxylic acids and inorganic acids, such as, for example, oxalic acid, maleic acid, phosphoric acid, fumaric acid and trifluoroacetic acid. Preference is given to trifluoroacetic acid.

The acid is generally employed in an amount of from 0.1 mol to 5 mol, preferably 1 mol, based on 1 mol of the compounds of the general formula (XIX).

The reaction is generally carried out at atmospheric pressure. However, it is also possible to carry out the reaction at elevated or reduced pressure.

The reaction is generally carried out at the reflux temperature of the solvent in question.

The compounds of the general formulae (XV) and (XIX) are known per se or can be prepared by customary methods.

The compounds of the general formula (XVIII) are novel and can be prepared by initially preparing, by reaction of the compounds of the general formula (XX):

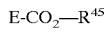

(XX), in which
E is as defined above
and
$R^{45}$ represents $C_1$–$C_4$-alkyl
with compounds of the general formula (XXI):

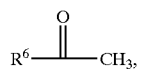

(XXI)

in which
$R^6$ is as defined above
in a solvent in the presence of 18-crown-6 ether, the compounds of the general formula (XXII):

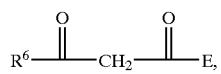

(XXII)

in which
$R^6$ and E are as defined above,
followed by reaction with ammonium acetate in inert solvents.

Suitable solvents for the first step of the process are the abovementioned ethers and hydrocarbons, preference being given to tetrahydrofuran.

Suitable solvents for the reaction with the compounds of the general formula (XXII) are alcohols, such as, for example, methanol, ethanol, propanol or isopropanol. Preference is given to ethanol.

All steps of the process are carried out at the respective reflux temperature of the solvent in question and at atmospheric pressure.

Some of the compounds of the general formulae (XX) and (XXI) are known, or they can be prepared by known methods.

Some of the compounds of the general formula (XXII) are novel species, and they can be prepared as described above.

The compounds of the general formulae (I) and (Ia) according to the invention have a pharmacological activity spectrum which could not have been foreseen.

The compounds of the general formula (I) and (Ia) according to the invention have useful pharmacological properties which are superior when compared to the prior art, in particular, they are highly effective inhibitors of the cholesterol ester transfer protein (CETP) and they stimulate the reverse cholesterol transport. The active compounds according to the invention effect a reduction in the LDL cholesterol level in the blood and simultaneously increase the HDL cholesterol level. They can therefore be used for the treatment and prevention of hypolipoproteinaemia, dyslipidaemias, hypertriglyceridaemias, hyperlipidaemias or arteriosclerosis.

The pharmacological activity of the substances according to the invention was determined in the following test:

CETP Inhibition Test

Preparation of CETP

CETP is obtained in partially purified form from human plasma by differential centrifugation and column chromatography and used for the test. For this purpose, human plasma is adjusted to a density of 1.21 g per ml using NaBr and centrifuged at 50,000 rpm at 4° C. for 18 h. The bottom fraction (d>1.21 g/ml) is applied to a Sephadex®Phenyl-Sepharose 4B (Pharmacia) column, washed with 0.15 m NaCl/0.001 m TrisHCl pH 7.4 and subsequently eluted using dist. water. The CETP-active fractions are pooled, dialysed against 50 mM Na-acetate pH 4.5 and applied to a CM-Sepharose® (Pharmacia) column. Elution is subsequently carried out using a linear gradient (0–1 M NaCl). The pooled CETP fractions are dialysed against 10 mM TrisHCl pH 7.4 and subsequently purified further by chromatography over a Mono Q® column (Pharmacia).

Preparation of Radioactively Labelled HDL 50 ml of fresh human EDTA plasma are adjusted to a density of 1.12 using NaBr and centrifuged at 4° C. in a Ty 65 rotor at 50,000 rpm for 18 h. The upper phase is used to obtain cold LDL. The lower phase is dialysed against 3*4l of PDB buffer (10 mM Tris/HCl pH 7.4, 0.15 mM NaCl, 1 mM EDTA, 0.02% $NaN_3$). Per 10 ml volume of retained material, 20 μl of 3H-cholesterol (Dupont NET-725; 1 μC/μl, dissolved in ethanol!) are subsequently added, and the mixture is incubated at 37° C. under $N_2$ for 72 h.

The mixture is then adjusted to a density of 1.21 using NaBr and centrifuged in a Ty 65 rotor at 20° C. and 50,000 rpm for 18 h. The upper phase is collected and the lipoprotein fractions are purified by gradient centrifugation. To this end, the isolated labelled lipoprotein fraction is adjusted to a density of 1.26 using NaBr. In each case 4 ml of this solution are covered in centrifuge tubes (SW 40 rotor) with 4 ml of a solution of a density of 1.21 and 4.5 ml of a solution of 1.063 (density solutions of PDB buffer and NaBr), and the tubes are subsequently centrifuged in an SW 40 rotor at 38,000 rpm and 20° C. for 24 h. The intermediate layer which is found between a density of 1.063 and a density of 1.21 and which contains the labelled HDL is dialysed against 3*100 volume of PDB buffer at 4° C.

The retained material contains radioactively labelled $^3$H-CE-HDL, which is used for the test adjusted to approximately $5 \times 10^6$ cmp per ml.

CETP Test

To test the CETP activity, the transfer of $^3$H-cholesterol ester from human HD-lipoproteins to biotinylated LD-lipoproteins is measured.

The reaction is terminated by addition of Streptavidin-SPA® beads (Amersham) and the transferred radioactivity is directly determined in a liquid scintillation counter.

In the assay mixture, 10 μl of HDL-$^3$H-cholesterol ester (~50,000 cpm) with 10 μl of Biotin-LDL (Amersham) in 50 mM Hepes/0.15 m NaCl/0.1% bovine serum albumin/0.05% $NaN_3$ pH 7.4 are incubated with 10 μl of CETP (1 mg/ml) and 3 μl of a solution of the substance to be tested (dissolved in 10% DMSO/1% BSA) at 37° C. for 18 h. 200 μl of the SPA streptavidin bead solution (TRKQ 7005) are subsequently added, the mixture is incubated with shaking for another 1 h and subsequently measured in a scintillation counter. The controls used are corresponding incubations with 10 µl of buffer, 10 µl of CETP at 4° C. and 10 µl of CETP at 37° C.

The activity which is transferred in the control experiments with CETP at 37° C. is classified as 100% transfer. The substance concentration at which this transfer is reduced by half is stated as the $IC_{50}$ value.

In Table A below, the $IC_{50}$ values (mol/l) for CETP inhibitors are given:

TABLE A

| Example No. | $IC_{50}$ value (mol/l) |
|---|---|
| 1 | $1 \times 10^{-8}$ |

Ex Vivo Activity of the Compounds According to the Invention

Syrian gold hamsters, which have been bred in our own laboratory, are anesthetized after 24 hours of fasting (0.8 mg/kg of atropine, 0.8 mg/kg of Ketavet® s.c., 30' later 50 mg/kg of Nembutal i.p.). The jugular vein is subsequently exposed and cannulated. The test substance is dissolved in a suitable solvent (usually adalate placebo solution: 60 g of glycerol, 100 ml of $H_2O$, ad 1000 ml PEG-400) and administered to the animals via a PE catheter, which is introduced into the jugular vein. The same volume of solvent without test substance is administered to the control animals. The vein is subsequently tied off and the wound is closed.

The test substances can also be administered p.o. by dissolving the substances in DMSO and suspending them in 0.5% tylose and administering them perorally using a pharyngeal tube. Identical volumes of solvent without test substance are administered to the control animals.

At different intervals—up to 24 hours after administration—blood samples are taken from the animals by puncture of the retro-orbital venous plexus (approximately 250 µl). Coagulation is completed by incubation at 4° C. overnight, and the samples are subsequently centrifuged at 6000×g for 10 minutes. The CETP activity is determined in the resulting serum using the modified CETP test. The transfer of $^3H$-cholesterol ester from HD-lipoproteins to biotinylated LD-lipoproteins is measured as described above for the CETP test.

The reaction is terminated by addition of Streptavidin-$SPA^R$ beads (Amersham), and the transferred radioactivity is directly determined in a liquid scintillation counter.

The test protocol is carried out as described under "CETP test". However, to test the serum, only 10 µl of CETP are replaced by 10µl of the appropriate serum samples. Corresponding incubations of sera of untreated animals serve as controls.

The activity that is transferred in the control experiments using control sera is classified as 100% transfer. The substance concentration at which this transfer is reduced by half is stated as the $ED_{50}$ value.

In Vivo Activity of the Compounds According to the Invention

In experiments for determining the oral activity on lipoproteins and triglycerides, test substance, dissolved in DMSO and suspended in 0.5% tylose, is administered perorally by means of a pharyngeal tube to Syrian gold hamsters which have been bred in our own laboratory. To determine the CETP activity, blood samples (approximately 250 µl) are taken by retro-orbital puncture prior to the start of the experiment. The test substances are subsequently administered perorally using a pharyngeal tube. Identical volumes of solvent without test substance are administered to the control animals. Subsequently, the animals have to fast and at different intervals—up to 24 hours after administration of the substances—blood samples are taken by puncture of the retro-orbital venous plexus.

Coagulation is completed by incubation at 4° C. overnight, and the samples are subsequently centrifuged at 6000×g for 10 minutes. The content of cholesterol and triglycerides in the resulting serum is determined using modified commercially available enzyme tests (cholesterol enzymatic 14366 Merck, triglycerides 14364 Merck). Serum is diluted in a suitable manner with normal saline solution.

100 µl of serum dilution and 100 µl of test substance are transferred into 96-well plates and incubated at room temperature for 10 minutes. The optical density is subsequently determined at a wavelength of 492 nm using an automatic plate reader. The triglyceride and cholesterol concentrations of the samples are determined with the aid of a standard curve measured in parallel.

The determination of the HDL-cholesterol content is carried out after precipitation of the ApoB-containing lipoproteins using a reagent mixture (Sigma 352-4 HDL cholesterol reagent) in accordance with the instructions of the manufacturer.

In Vivo Activity in Transgenic hCETP Mice

The substances to be tested were administered to transgenic mice, which were bred in our own laboratory (Dinchuck, Hart, Gonzalez, Karmann, Schmidt, Wirak; BBA (1995), 1295, 301), via the feed. Prior to the beginning of the experiment, blood samples were taken retro-orbitally from the mice to determine cholesterol and triglycerides in the serum. The serum was obtained as described above for hamsters by incubation at 4° C. overnight and subsequent centrifugation at 6000×g. After one week, blood samples were again taken from the mice to determine lipoproteins and triglycerides. The change of the measured parameters are expressed as a change in per cent based on the initial value.

The invention furthermore relates to the combination of hetero-tetrahydroquinolines of the general formula (I) with a glucosidase and/or amylase inhibitor for the treatment of familial hyperlipidaemias, of obesity (adipositas) and of diabetes mellitus. Glucosidase and/or amylase inhibitors in the context of the present invention are, for example, acarbose, adiposine, voglibose, miglitol, emiglitate, MDL-25637, camiglibose (MDL-73945), tendamistate, AI-3688, trestatin, pradimicin-Q and salbostatin.

Preference is given to the combination of acarbose, miglitol, emiglitate or voglibose with one of the abovementioned compounds of the general formula (I) according to the invention.

Furthermore, the compounds according to the invention can be combined with cholesterol-lowering vastatines or ApoB-lowering principles, in order to treat dyslipidaemias, combined hyperlipidaemias, hypercholesterolaemias or hypertriglyceridaemias.

The abovementioned combinations can also be used for primary or secondary prevention of coronary heart diseases (for example myocardial infarction).

Vastatines in the context of the present invention are, for example, lovastatin, sinivastatin, pravastatin, fluvastatin, atorvastatin and cerivastatin. ApoB-lowering agents are, for example, MTP inhibitors.

Preference is given to the combination of cerivastatin or ApoB inhibitors with one of the abovementioned compounds of the general formula (I) according to the invention.

The novel active compounds can be converted in a known manner into the customary formulations, such as tablets, coated tablets, pills, granules, aerosols, syrups, emulsions, suspensions and solutions, using inert, non-toxic, pharmaceutically suitable carriers or solvents. In this case the therapeutically active compound should in each case be present in a concentration of from approximately 0.5 to 90% by weight of the total mixture, i.e. in amounts which are sufficient in order to achieve the dosage range indicated.

The formulations are prepared, for example, by extending the active compounds using solvents and/or carriers, if appropriate using emulsifiers and/or dispersants, it optionally being possible, for example, to use organic solvents as auxiliary solvents if the diluent used is water.

Administration is carried out in a customary manner, intravenously, orally, parenterally or perlingually, in particular orally.

In the case of parenteral administration, solutions of the active compound can be used by employing suitable liquid carrier materials.

In general, it has proved advantageous, in the case of intravenous administration, to administer amounts of from approximately 0.001 to 1 mg/kg, preferably approximately 0.01 to 0.5 mg/kg, of body weight to achieve effective results, and in the case of oral administration the dosage is approximately 0.01 to 20 mg/kg, preferably 0.1 to 10 mg/kg, of body weight.

In spite of this, if appropriate it may be necessary to depart from the amounts mentioned, namely depending on the body weight or on the type of administration route, on the individual reaction towards the medicament, the manner of its formulation and the time at or interval during which administration takes place. Thus, in some cases it may be adequate to manage with less than the abovementioned minimum amount, while in other cases the upper limit mentioned has to be exceeded. In the case of the administration of relatively large amounts, it may be advisable to divide these into several individual doses over the course of the day Abbreviations Used:

Cy=Cyclohexane
EA=Ethyl acetate
PE=Petroleum ether
THF=Tetrahydrofuran
DAST=Dimethylaminosulphur trifluoride
PTA=para-toluenesulphonic acid
PDC=Pyridinium dichromate
PE/EA=Petroleum ether/ethyl acetate
Tol=Toluene Starting Materials

EXAMPLE I

2-Cyclopentyl-7,7-dimethyl-4-(3-thienyl)-3-(4-trifluoromethylbenzoyl)-1,4,5,6,7,8-hexahydro-quinolin-5-one

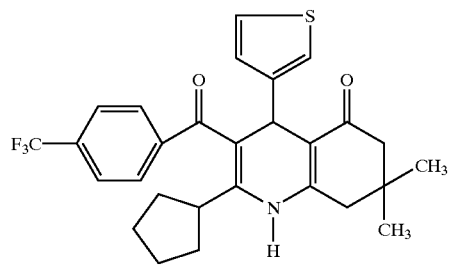

1.425 g (5.03 mol) of 3-amino-3-cyclopentyl-1-(4-trifluoromethylphenyl)-propenone are suspended in 25 ml of diisopropyl ether. 740 mg (5.28 mol) of dimedone, 0.39 ml (5.03 mol) of trifluoroacetic acid and then 592 mg (5.28 mol) of thiophen-3-aldehyde are added. The mixture is heated at reflux for 2 hours, which immediately gives a yellow solution from which, after 30 minutes, product precipitates out. The mixture is cooled and the product is filtered off with suction and washed with diisopropyl ether. The product is recrystallized from acetonitrile.

Yield: 741 mg, m.p. 228–229° C.

The mother liquor gives another 230 mg of pure product.

The compounds listed in Table I are prepared analogously to the procedure of Example I:

TABLE I

| Ex. No. | Structure | m.p.: (° C.) |
|---|---|---|
| II | 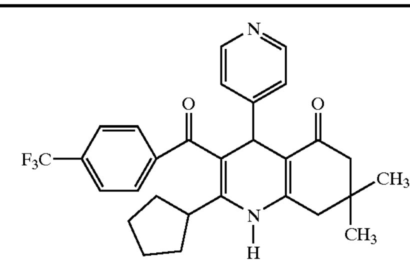 | 144–47 |
| III | 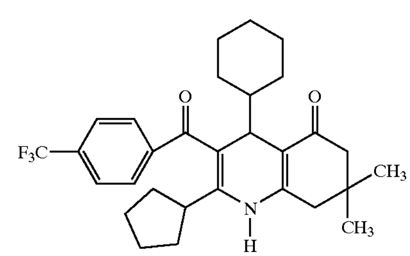 | 200–206 |

PREPARATION EXAMPLES

Example 1

2-Cyclopentyl-7,7-dimethyl-4-(3-thienyl)-3-(4-trifluoromethylbenzoyl)-5,6,7,8-tetrahydro-quinolin-5-one

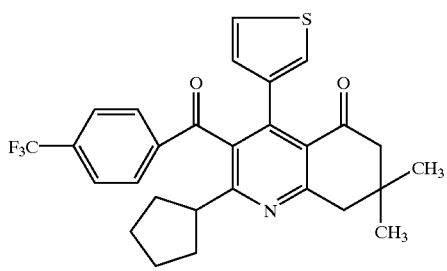

1.21 g (2.42 mmol) of the compound from Example I are dissolved in 35 ml of dichloromethane and, after addition of 6.8 g of manganese dioxide, stirred for 2 hours. The mixture is filtered off with suction using Celite as a filtration aid and is concentrated. The evaporation residue is stirred with acetonitrile, filtered off with suction and washed with acetonitrile. This gives 1.045 g of crystals of m.p.: 236–238° C.

The compounds listed in Table 1 are prepared analogously to the procedure of Example 1:

TABLE 1

| Ex. No. | Structure | m.p. (° C.) |
|---|---|---|
| 2 | 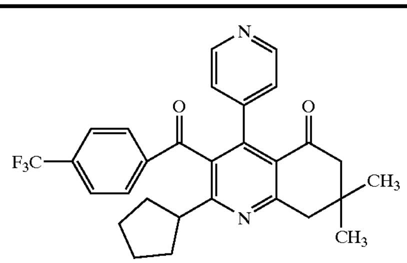 | 221–224 |
| 3 | 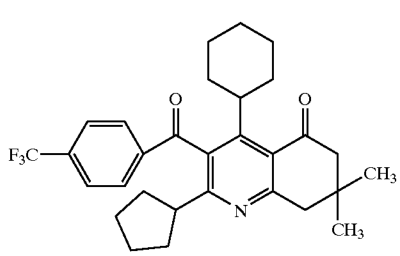 | 185–186 |

Example 4

2-Cyclopentyl-5-hydroxy-7,7-dimethyl-4-(3-thienyl)-3-(4-trifluoromethylbenzoyl)-5,6,7,8-tetrahydroquinoline

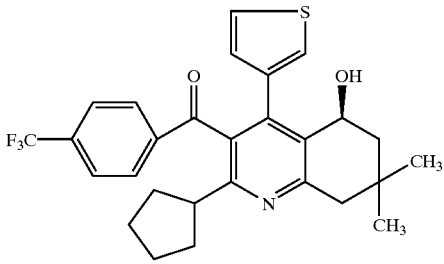

(1R,2S)-Aminoindan-2-ol are suspended in 0.4 ml of THF. At RT, N,N-boranediethylaniline complex (Aldrich) are added dropwise. All is dissolved and stirred at RT for 1 hour. The mixture is then stirred at 0° C. for 15 minutes. The compound from Example 1 is dissolved in 16 ml of THF and added dropwise at from 0 to 5° C. over a period of 10 minutes. The mixture is then stirred at 0° C. for 30 min and at RT for 4 hours. At from −10° C. to 0° C., 35 ml of 1,2 ethanediol are carefully added dropwise, the mixture is stirred for 30 minutes and concentrated, the residue is dissolved in ethyl acetate, the solution is washed with 1 N HCl, then with sat. sodium bicarbonate solution, then with sat. sodium chloride solution, dried over sodium sulphate, filtered and concentrated. This gives 1.17 g of a crystalline compound. The compound is dissolved in hot cyclohexane and the mixture is filtered off. On cooling, the compound crystallizes out. The mixture is filtered off with suction and the compound is washed and dried at 70° C. under reduced pressure.

Yield: 0.7 g

Concentration of the mother liquor (column: toluene: ethyl acetate 20.1), dissolving the residue in methylene chloride and reconcentrating the solution gives a further 0.27 g of crystals.

Overall yield: 970 mg (87.3%) of m.p.: 179–182° C.

Example 5

5-tertButyldimethylsilyloxy-2-cyclopentyl-7,7-dimethyl-4-(3-thienyl)-3-(4-trifluoromethylbenzoyl)-5,6,7,8-tetrahydroquinoline

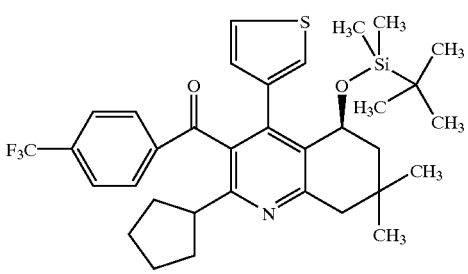

Under argon, 0.8 g (1.6 mmol) of the compound from Example 4 is dissolved in 6.4 ml of toluene and, at from −5° to -10° C. admixed dropwise with 0.69 g (6.4 mmol) of 2,6-lutidine. The mixture is stirred for 15 minutes. At the same temperature, 0.86 g (3.2 mmol) of tertbutyldimethylsilyl trifluoromethanesulphonate in 1.2 ml of toluene is then added dropwise. The mixture is stirred at from −5° C. to −10° C. for 15 minutes and then at room temperature for 2 hours.

The mixture is diluted with toluene and washed successively with 2.6 ml of 10% ammonium chloride solution, 7 times with in each case 3.5 ml of 0.1 N HCl, once with 1.5 ml of sat. sodium bicarbonate solution and once with 3.5 ml of sat. sodium chloride solution. The mixture is then dried and concentrated and concentrated once with ethanol.

This gives 1.0 g The product is recrystallized from a little ethanol, filtered off with suction, washed and dried at 60° C. under reduced pressure.

Yield: 716 mg, m.p. 147–148° C.

The mother liquor is concentrated and the residue is treated with ethanol and filtered off with suction. This gives another 60 mg.

Example 6

5-(S)-tertButyldimethylsilyloxy-2-cyclopentyl-7,7-dimethyl-4-(3-thienyl)-3-[(R)-hydroxy-(4-trifluoromethylphenyl)]methyl-5,6,7,8-tetrahydroquinoline

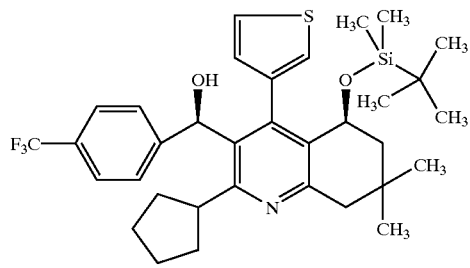

0.69 g (1.124 mmol) of the compound from Example 5 is dissolved in 5 ml of toluene; at 0° C., 1.40 g (4.496 mmol) of RED-Al are added dropwise and the mixture is stirred at 0° C. for 30 minutes and at RT for 1 hour. At 0° C., 0.85 ml of methanol is slowly added dropwise, and the yellow solution is stirred at 0° C. for 30 minutes. 0.73 ml of a 20% strength potassium sodium tartrate solution is then added dropwise, the mixture is filtered off with suction, the filtrate is washed with toluene and a little 20% strength potassium sodium tartrate solution, separated off, washed once with sat. sodium bicarbonate solution and twice with sat. sodium chloride solution, dried over sodium sulphate and concentrated. This gives 850 mg of an oil which comprises the two possible diastereomers which are separated on a 400 ml silica gel column. The product is eluted with petroleum ether, petroleum ether/ethyl acetate 20:1, 10:1.

This gives 86.2 mg of the wrong diastereomer and 356.2 mg of the right diastereomer.

Example 7

5-(S)-tertButyldimethylsilyloxy-2-cyclopentyl-7,7-dimethyl-3-[5-fluoro-(4-trifluoro-methylphenyl)-methyl]-4-(3-thienyl)-5,6,7,8-tetrahydroquinoline

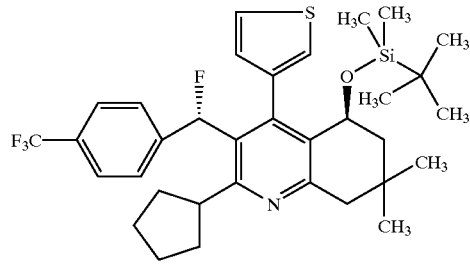

320 mg (0.52 mmol) of the compound from Example 6 are dissolved in 7 ml of dichloromethane and, at −15° C., treated with 140 mg (0.86 mmol) of DAST. After 30 minutes, the reaction is carried out at from −15° C. to −10° C., methylene chloride and water are added, the phases are separated, the aqueous phases extracted once with methylene chloride, and the organic phases are washed once with sat. sodium chloride solution and with a little sat. sodium bicarbonate solution, dried and concentrated.

Crystallization is carried out using methanol. The product is filtered off with suction and washed.

Yield: 57.8 mg of m.p.: 171–172° C.

Example 8

2-Cyclopentyl-3-[fluoro-(4-trifluoromethylphenyl)methyl]-5-hydroxy-7,7-dimethyl-4-(3-thienyl)-5,6,7,8-tetrahydroquinoline

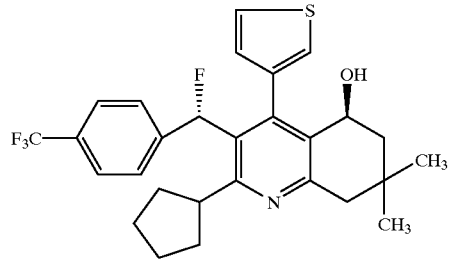

111 mg (0.18 mmol) of the compound from Example 7 are dissolved in 1.4 ml of methanol and admixed with 0.9 ml of THF and 0.98 ml of 5 N hydrochloric acid. The mixture is stirred at 40° C. for 4 hours. The mixture is concentrated, admixed with water, ammonia solution and ethyl acetate, the phases are separated and the aqueous phases extracted once with ethyl acetate. The organic phases are washed once with sodium chloride solution, dried and concentrated. this gives 82 mg as an oil.

The product is dissolved in petroleum ether and a little methylene chloride and applied to a column, eluted with petroleum ether: ethyl acetate 30.1, 20.1, 10.1, and 2 fractions are concentrated.

The crystalline solid is filtered off with suction with a little n-heptane and dried under reduced pressure.

This gives 37.1 mg (41% of theory) of a colourless substance of m.p.: 157–159° C.

Example 9

2-Cyclopentyl-5-hydroxy-7,7-dimethyl-4-(3-thienyl)-3-(trifuoromethylbenzyl)-5,6,7,8-tetrahydroquinoline

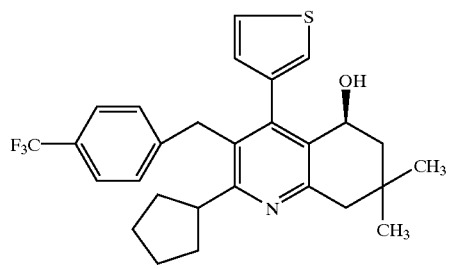

20 mg (0.04 mmol) of the compound from Example 8 are dissolved in 3 ml of toluene and, at −20° C., admixed with 0.27 ml of Dibal-H in tolol. The mixture is stirred at −20° C. for 2 hours. The mixture is admixed with 10 ml of 20% potassium sodium tartrate solution and ethyl acetate and stirred for some time, the phases are separated, the aqueous phase is extracted 2× with ethyl acetate, and the organic phases are dried and concentrated.

17 mg of the title compound are dissolved in methylene chloride, applied to a column and eluted with toluene.

FR 1–1:5.5 mg NMR $R_f$ value: TLC aluminum foil silica gel 60 $F_{254}$, layer thickness 0.2 mm=0.40 (mobile phase: petroleum ether/ethyl acetate 10:1)

$R_f$=0.45; mobile phase toluene/ethyl acetate 10:1.

The compounds listed in Table 1 are prepared analogously to the procedures given above:

| Ex. No. | Structure | Isomer | $R_f$ |
|---|---|---|---|
| 10 | 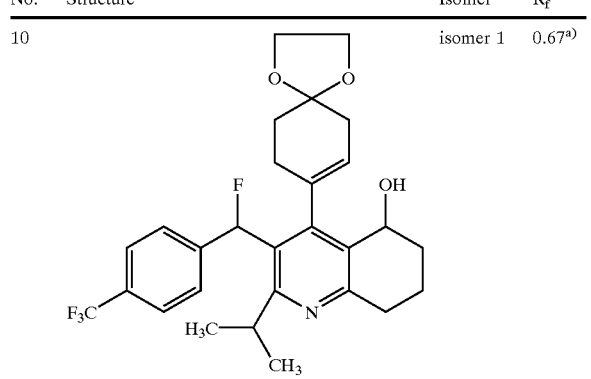 | isomer 1 | 0.67[a] |
| 11 | (structure continued) | isomer 2 | 0.52[a] |

[a] EtOAc/petroleum ether 1:1

What is claimed is:
1. A hetero-tetrahydroquinoline according to the formula:

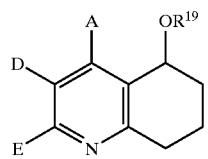

in which A represents a radical of the formula:

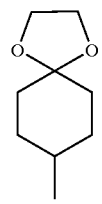

and wherein
D represents aryl having 6 to 10 carbon atoms, which is optionally substituted one or more times by phenyl, nitro, halogen, trifluoromethyl, trifluoromethoxy,
  or
  represents a radical of the formula:

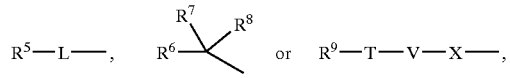

in which
  $R^5$, $R^6$ and $R^9$ independently represent cycloalkyl having 3 to 6 carbon atoms, or aryl having 6 to 10 carbon atoms,
  which are optionally substituted up to 5 times by identical or different substituents from the group consisting of halogen, trifluoromethyl, nitro, hydroxyl, cyano, carboxyl, trifluoromethoxy, and straight-chain or branched acyl having up to 6 carbon atoms, straight-chain or branched alkyl having up to 6 carbon atoms, straight-chain or branched alkylthio having up to 6 carbon atoms, straight-chain or branched alkylalkoxy having up to 6 carbon atoms, straight-chain or branched alkoxy having up to 6 carbon atoms or straight-chain or branched alkoxy-carbonyl having up to 6 carbon atoms, aryl having 6 to 10 carbon atoms, trifluoromethyl-substituted aryl having 6 to 10 carbon atoms, radicals of the formula —$OR^{10}$, radicals of the formula —$SR^{11}$, radicals of the formula —$SO_2R^{12}$ and radicals of the formula: —$NR^{13}R^{14}$, in which $R^{10}$, $R^{11}$ and $R^{12}$ represent aryl having 6 to 10 carbon atoms which is substituted up to 2 times by identical or different substituents selected from the group consisting of phenyl, halogen and straight-chain or branched alkyl having up to 6 carbon atoms;

$R^{13}$ and $R^{14}$ represent hydrogen, phenyl, or straight-chain or branched alkyl having up to 6 carbon atoms;

$R^7$ represents hydrogen or halogen, and $R^8$ represents hydrogen, halogen, azido, trifluoromethyl, hydroxyl, trifluoromethoxy, straight-chain or branched alkoxy having up to six carbon atoms, straight-chain or branched alkyl having up to six carbon atoms, or a radical of the formula —$NR^{15}R^{16}$, in which $R^{15}$ and $R^{16}$ are identical or different and represent hydrogen, phenyl, or
straight-chain or branched alkyl having up to 6 carbon atoms,
or $R^7$ and $R^8$ together form a radical of the formula =O or =$NR^{17}$, in which $R^{17}$ represents hydrogen or straight-chain or branched alkyl having up to 6 carbon atoms, straight-chain or branched alkoxy having up to 6 carbon atoms or straight-chain or branched acyl having up to 6 carbon atoms, L represents a straight-chain or branched alkylene having up to 8 carbon atoms or straight-chain or branched alkenylene chain having up to 8 carbon atoms, each of which alkylene or alkenylene are optionally substituted up to 2 times by hydroxyl;

T and X are identical or different and represent a straight-chain or branched alkylene chain having up to 8 carbon atoms,
or T or X represents a bond;

V represents an oxygen or sulfur atom or represents an —$NR^{18}$ group, in which $R^{18}$ represents hydrogen, straight-chain or branched alkyl having up to 6 carbon atoms or phenyl, E represents cycloalkyl having 3 to 8 carbon atoms, or
represents straight-chain or branched alkyl having up to 8 carbon atoms which is optionally substituted by cycloalkyl having 3 to 8 carbon atoms or hydroxyl;
or
represents phenyl, which is optionally substituted by halogen or trifluoromethyl; and $R^{19}$ represents hydrogen; or represents cycloalkyl having 3 to 7 carbon atoms; or
represents straight-chain or branched silylalkyl having up to 8 carbon atoms;
or represents straight-chain or branched alkyl having up to 8 carbon atoms,
which alkyl is optionally substituted by hydroxyl; or straight-chain or branched alkoxy having up to 6 carbon atoms; a radical of the formula —$OR^{22}$; or phenyl, which phenyl is optionally substituted by halogen, nitro, trifluoromethyl, trifluoromethoxy, phenyl or tetrazole-substituted phenyl;

in which $R^{22}$ represents straight-chain or branched acyl having up to 4 carbon atoms or benzyl;

or $R^{19}$ represents straight-chain or branched acyl having up to 20 carbon atoms or benzoyl which is optionally substituted by halogen, trifluoromethyl, nitro or trifluoromethoxy, or
represents straight-chain or branched fluoroacyl having up to 8 carbon atoms and 9 fluorine atoms
or a salt of said compound or or an N-oxide of said compound or said salt.

2. The hetero-tetrahydroquinoline according to claim 1, in which

A is optionally substituted up to 2 times by one or more substituents selected from the group consisting of fluorine, chlorine, bromine, amino, hydroxyl, trifluoromethyl, trifluormethoxy, straight-chain or branched alkyl having up to 6 carbon atoms, and straight-chain or branched alkoxy having up to 6 carbon atoms;

D represents aryl having 6 to 10 carbon atoms, which is optionally substituted one or more times by phenyl, nitro, chlorine, bromine, fluorine, trifluoromethyl, trifluoromethoxy, or represents a radical of the formula:

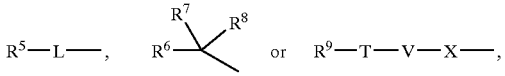

in which, $R^5$, $R^6$ and $R^9$ independently represent cyclopropyl, cyclopentyl, cyclohexyl, phenyl or napththyl, each of which are optionally substituted up to 3 times by identical or different substituents selected from the group consisting of fluorine, chlorine, bromine, trifluoromethyl, hydroxyl, cyano, carboxyl, trifluoromethoxy, straight-chain or branched acyl having up to 4 carbon atoms, straight-chain or branched alkyl having up to 4 carbon atoms, straight-chain or branched alkylthio having up to 4 carbon atoms, straight-chain or branched alkylalkoxy having up to 4 carbon atoms, straight-chain or branched alkoxycarbonyl having up to 4 carbon atoms, trifluoromethyl-substituted phenyl and phenyl;

$R^7$ represents hydrogen, fluorine, chlorine or bromine; and $R^8$ represents hydrogen, fluorine, chlorine, bromine, azido, trifluoromethyl, hydroxyl, trifluoromethoxy, straight-chain or branched alkoxy having up to 5 carbon atoms, or straight-chain or branched alkoxy alkyl having up to 5 carbon atoms or a radical of the formula —$NR^{15}R^{16}$, in which $R^{15}$ and $R^{16}$ are identical or different and represent hydrogen, phenyl or straight-chain or branched alkyl having up to 4 carbon atoms, or $R^7$ and $R^8$ together form a radical of the formula =O or =$NR^{17}$, in which $R^{17}$ represents hydrogen, straight-chain or branched alkyl having up to 4 carbon atoms, straight-chain or branched alkoxy having up to 4 carbon atoms, straight-chain or branched acyl having up to 4 carbon atoms;

L represents a straight-chain or branched alkylene having up to 6 carbon atoms, or straight-chain or branched alkenylene having to 6 carbon atoms, each of which alkylene or alkenylene are optionally substituted up to 2 times by hydroxyl;

T and X are identical or different and represent a straight-chain or branched alkylene chain having up to 6 carbon atoms;

or

T or X represents a bond,

V represents an oxygen or sulfur atom or represents an —$NR^{18}$ group;

in which $R^{18}$ represents hydrogen or straight-chain or branched alkyl having up to 4 carbon atoms or phenyl, E represents cyclopropyl, cyclobutyl, cylcopentyl, cyclohexyl, cycloheptyl, or represents straight-chain or branched alkyl having up to 6 carbon atoms which is optionally substituted by cyclopropyl, cylcopentyl, cyclohexyl, cycloheptyl, or hydroxyl; or represents phenyl which is optionally substituted by fluorine, chlorine or trifluoromethyl;

and, $R^{19}$ represents hydrogen, or represents cyclopropyl, cyclopentyl, cyclohexyl, or represents straight-chain or branched silylalkyl having up to 7 carbon atoms, or represents straight-chain or branched alkyl having up to 6 carbon atoms which is optionally substituted by hydroxyl, straight-chain or branched alkoxy having up to 4 carbon atoms, a radical of the formula —$OR^{22}$ or by phenyl which is optionally substituted by fluorine, chlorine, bromine, nitro, trifluoromethyl, trifluoromethoxy or by phenyl or tetrazole-substituted phenyl, in which $R^{22}$ represents straight-chain or branched acyl having up to 3 carbon atoms or benzyl;

or, $R^{19}$ represents straight-chain or branched acyl having up to 18 carbon atoms or benzoyl which is optionally substituted by fluorine, chlorine, bromine, trifluoromethyl, nitro or trifluoromethoxy, or represents straight-chain or branched fluoroacyl having up to 6 carbon atoms, or a salt of said compound or an N-oxide of said compound or said salt.

3. The hetero-tetrahydroquinoline according to claim 1, wherein

D represents aryl having 6 to 10 carbon atoms which is optionally substituted one or more times by nitro, trifluoromethyl, trifluoromethoxy, fluorine, chlorine or bromine, or represents a radical of the formula:

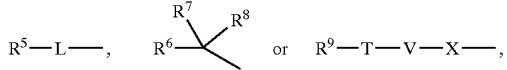

in which $R^5$, $R^6$ and $R^9$ independently represent cyclopropyl, cyclopentyl or cyclohexyl, phenyl, or naphthyl each of which are optionally substituted up to 2 times by identical or different substituents from the group consisting of fluorine, chlorine, trifluoromethyl, hydroxyl, cyano, carboxyl, trifluoromethoxy, straight-chain or branched alkyl having up to 4 carbon atoms, straight-chain or branched alkylthio having up to 4 carbon atoms, straight-chain or branched alkylalkoxy having up to 4 carbon atoms, straight-chain or branched alkoxy having up to 4 carbon atoms, or straight-chain or branched alkoxycarbonyl having up to 4 carbon atoms;

$R^7$ represents hydrogen or fluorine;

and $R^6$ represents hydrogen, fluorine, chlorine, bromine, azido, trifluoromethyl, hydroxyl, trifluoromethoxy, or straight-chain or branched alkoxy or straight chain or branched alkyl having up to 4 carbon atoms or a radical of the formula —$NR^{15}R^{16}$, in which $R^{15}$ and $R^{16}$ are identical or different and represent hydrogen or straight-chain or branched alkyl having up to 3 carbon atoms, or $R^7$ and $R^8$ together form a radical of the formula =O, L represents a straight-chain or branched alkylene or alkenylene each having up to 5 carbon atoms, each alkylene or alkenylene are optionally substituted up to 2 times by hydroxyl;

T and X are identical or different and represent a straight-chain or branched alkylene chain having up to 3 carbon atoms;

or

T or X represents a bond;

V represents an oxygen or sulfur atom or represents a group of the formula —$NR^{18}$ in which $R^{18}$ represents hydrogen or straight-chain or branched alkyl having up to 3 carbon atoms;

E represents cyclopropyl, cyclopentyl or cyclohexyl or phenyl which is optionally substituted by fluorine or trifluoromethyl, or represents straight-chain or branched alkyl having up to 4 carbon atoms which is optionally substituted by hydroxyl; or $R^{19}$ represents hydrogen;

or represents cyclopropyl, cyclopentyl or cyclohexyl;

or represents straight-chain or branched acyl having up to 15 carbon atoms or benzoyl which is optionally substituted by fluorine, chlorine, bromine, trifluoromethyl, nitro or trifluoromethoxy; or represents a radical of the formula —$Si(CH_3)_2C(CH_3)_3$;

or a salt of said compound or an N-oxide of said compound represents straight-chain or branched fluoroacyl having up to 8 carbon atoms and 9 fluorine atoms or a salt of said compound or or an N-oxide of said compound or said salt.

4. The hetero-tetrahydroquinoline according to claim 1, wherein

D represents aryl having 6 to 8 carbon atoms which is optionally substituted one or more times by trifluoromethyl and/or fluorine, or trifluoromethoxy or, represents a radical of the formula:

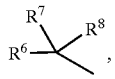

in which $R^6$ represents phenyl which is optionally substituted by fluorine, chlorine, trifluoromethyl, trifluoromethoxy, straight-chain or branched alkyl having up to 4 carbon atoms;

$R^7$ represents hydrogen or fluorine; and $R^8$ represents hydrogen, fluorine, chlorine, hydroxyl, methoxy; or $R^7$ and $R^8$ together represent a radical of the formula =O, E represents cyclopropyl, cyclopentyl, or cyclohexyl, or straight-chain or branched alkyl having up to 4 carbon atoms which is optionally substituted by hydroxyl;

or a salt of said compound or an N-oxide of said compound or said salt.

5. A pharmaceutical composition comprising a pharmaceutically acceptable carrier and an effective amount of the hetero-tetrahydroquinoline compound of claim 1, or a, salt or N-oxide, thereof.

6. A method for treating hyperlipoproteinanaemia, said method comprising administering to a patient in need thereof an effective amount therefor of a composition according to claim 5.

7. A method for treating arteriosclerosis, said method comprising administering to a patient in need thereof an effective amount therefor of a composition according to claim 5.

8. A method for treating dyslipidaemia, said method comprising administering to a patient in need thereof an effective amount therefor of a composition according to claim 5.

* * * * *